(12) United States Patent
Adlard et al.

(10) Patent No.: US 11,602,538 B2
(45) Date of Patent: Mar. 14, 2023

(54) PROPHYLAXIS AND TREATMENT OF COGNITIVE DYSFUNCTION AND DECLINE

(71) Applicant: The Florey Institute of Neuroscience and Mental Health, Parkville (AU)

(72) Inventors: Paul Adlard, Coburg (AU); Stuart Portbury, Essendon (AU)

(73) Assignee: The Florey Institute of Neuroscience and Mental Health

(*) Notice: Subject to any disclaimer, the term of this patent is extended or adjusted under 35 U.S.C. 154(b) by 0 days.

(21) Appl. No.: 16/497,286

(22) PCT Filed: Mar. 29, 2018

(86) PCT No.: PCT/AU2018/050294
§ 371 (c)(1),
(2) Date: Sep. 24, 2019

(87) PCT Pub. No.: WO2018/176098
PCT Pub. Date: Oct. 4, 2018

(65) Prior Publication Data
US 2021/0121489 A1 Apr. 29, 2021

(30) Foreign Application Priority Data
Mar. 31, 2017 (AU) ................................ 2017901171

(51) Int. Cl.
| | | |
|---|---|---|
| A61K 31/7016 | (2006.01) | |
| A61P 25/28 | (2006.01) | |
| A61K 9/00 | (2006.01) | |
| A23L 33/125 | (2016.01) | |
| A23L 2/52 | (2006.01) | |

(52) U.S. Cl.
CPC ........ *A61K 31/7016* (2013.01); *A61K 9/0053* (2013.01); *A61P 25/28* (2018.01); *A23L 2/52* (2013.01); *A23L 33/125* (2016.08)

(58) Field of Classification Search
CPC ... A61P 25/28; A61K 9/0053; A61K 31/7016; A23L 33/125; A23L 2/52
USPC .......................................................... 514/53
See application file for complete search history.

(56) References Cited

U.S. PATENT DOCUMENTS

2009/0110746 A1* 4/2009 Gainer .................... A61P 19/02
424/601
2016/0303150 A1* 10/2016 Megiddo ............ A61K 31/7016

FOREIGN PATENT DOCUMENTS

| WO | WO 2008/133884 | 11/2008 |
| WO | WO 2009/058399 | 5/2009 |
| WO | WO 2010/022140 | 2/2010 |
| WO | WO 2016/133788 | 8/2016 |

OTHER PUBLICATIONS

Glossary of medical education terms, Institute of International Medical Education. http://www.iime.org/glossary.htm Accessed in Mar. 2013. (Year: 2013).*
Portbury SD, Hare DJ, Finkelstein DI, Adlard PA (2017) Trehalose improves traumatic brain injury-induced cognitive impairment. PLoS ONE 12(8): e0183683. (Year: 2017).*
Castillo, et al.; "Trehalose delays the progression of amyotrophic lateral sclerosis by enhancing autophagy in motoneurons"; Autophagy; vol. 9, No. 9, pp. 1308-1320 (Sep. 2013).
Du, et al.; "Trehalose rescues Alzheimer's disease phenotypes in APP/PSI transgenic mice"; Journal of Pharmacy and Pharmacology, vol. 65, No. 12, pp. 1753-1756 (2013).
Kara, et al.; "Trehalose induced antidepressant-like effects and autophagy enhancement in mice"; Psychopharmacology; vol. 229, pp. 367-375 (2013).
Li, et al.; "Trehalose Inhibits Protein Aggregation Caused by Transient Ischemic Insults Through Preservation of Proteasome Activity, Not via Induction of Autophagy"; Molecular Neurobiology, vol. 54, pp. 6857-6869 (2017).
Rodriguez-Navarro, J. et al. "Trehalose ameliorates dopaminergic and tau pathology in parkin deleted/tau overexpressing mice through autophagy activation", Neurobiology of Disease. vol. 39, No. 3, pp. 423-438 (2010).
Sarkar, S. et al. 2014 "Neuroprotective effect of the chemical chaperone, trehalose in a chronic MPTP-induced Parkinson's disease mouse model", NeuroToxicology, vol. 44, pp. 250-262.
Schaeffer, V. et al. 2012 "Stimulation of autophagy reduces neurodegeneration in a mouse model of human tauopathy", Brain, vol. 135, pp. 2169-2177.
Clark, et al.; "Autophagy is increased in mice after traumatic brain injury and is detectable in human brain after trauma and critical illness"; Autophagy; vol. 4, No. 1, pp. 88-90 (Jan. 1, 2008).
Sarkar, et al.; "Trehalose, a Novel mTOR-independent Autophagy Enhancer, Accelerates the Clearance of Mutant Huntingtin and α-Synuclein*"; The Journal of Biological Chemistry; vol. 282, No. 8, pp. 5641-5652 (Feb. 23, 2007).
Tang, et al.; "FGF2 Attenuates Neural Cell Death via Suppressing Autophagy after Rat Mild Traumatic Brain Injury"; Stem Cells International; vol. 2017, 14 pages (Oct. 17, 2017).
Yao, et al.; "Rosiglitazone exerts neuroprotective effects via the suppression of neuronal autophagy and apoptosis in the cortex following traumatic brain injury"; Molecular Medicine Reports; vol. 12, pp. 6591-6597 (2015).

* cited by examiner

*Primary Examiner* — Yih-Horng Shiao
(74) *Attorney, Agent, or Firm* — Bozicevic, Field & Francis LLP; Paula A. Borden (57) ABSTRACT

Provided in accordance with the present disclosure are methods for preventing or reducing cognitive dysfunction or decline associated with an acquired brain injury, for treating cognitive dysfunction or decline associated with an acquired brain injury, and for inducing or increasing neuroplasticity, the methods comprising administering to a subject in need thereof a therapeutically effective amount of trehalose.

17 Claims, 5 Drawing Sheets

PROPHYLAXIS AND TREATMENT OF COGNITIVE DYSFUNCTION AND DECLINE

CROSS-REFERENCE

This application is a national phase filing under 35 U.S.C. § 371 of PCT/AU2018/050294, filed Mar. 29, 2018, which claims the benefit of Australian Patent Application No. 2017901171, filed Mar. 31, 2017, which applications are incorporated herein by reference in their entirety.

FIELD OF THE ART

Embodiments of the present disclosure relate generally to methods for treating and preventing cognitive dysfunction or cognitive decline associated with acquired brain injury such as traumatic brain injury. The disclosure also relates to methods for increasing neuroplasticity following brain injury or in neurodegenerative disease.

BACKGROUND

Traumatic Brain Injury (TBI) is a condition that results from a mild to severe trauma or injury to the head. Initial assessment and diagnosis by clinicians is based on the Glasgow Coma Scale (GCS), which identifies TBI as mild, moderate or severe. TBI a major global health problem and represents the leading cause of mortality and disability in high-income countries. It is estimated that 1.7 million TBIs occur annually in the United States alone, and in 2006, 5.3 million people were living with long term or perpetual disabilities as a consequence of brain injury.

The causes of TBI are etiologically diverse, but largely include motor vehicle accidents, sports injuries, occupational hazards, physical violence and falls, all of which contribute to a significant public health burden. Concussion and related brain trauma resulting from contact sports such as boxing and various forms of football have been shown to culminate in subsequent behavioural disabilities and pathological effects, for example in the form of chronic traumatic encephalopathy. Similarly, military blast-induced TBI has also been shown to result in long-term cognitive deficits in affected individuals, and over 200,000 U.S. service members have been officially diagnosed with TBI since 2003.

TBI has been suggested to be a risk factor for the later development of neurodegenerative diseases such as Alzheimer's disease, Parkinson's disease and Amyotrophic Lateral Sclerosis. Even a single, mild TBI event is associated with an increased risk of progressive cognitive impairment, which can lead to dementia. Additionally, both depression and anxiety are common psychological manifestations following TBI.

Despite much effort, there is currently no therapeutic option available to ease or prevent some of the most debilitating symptoms that occur following TBI, such as cognitive dysfunction. In the face of the growing recognition of the incidences and cognitive effects of TBI, there remains a need for the development of effective treatment options.

SUMMARY OF THE DISCLOSURE

The present disclosure is predicated on the inventor's novel findings indicating that trehalose, a naturally occurring alpha-linked disaccharide comprising two molecules of glucose, may be efficacious in improving functional outcomes following TBI.

A first aspect of the present disclosure provides a method for preventing or reducing cognitive dysfunction or decline associated with an acquired brain injury in a subject, the method comprising administering to the subject a therapeutically effective amount of trehalose.

In an embodiment, the subject is at risk of an acquired brain injury. In a further embodiment the subject may have sustained an acquired brain injury.

A second aspect of the present disclosure provides a method for treating cognitive dysfunction or decline associated with an acquired brain injury in a subject, the method comprising administering to the subject a therapeutically effective amount of trehalose.

In embodiments of the first or second aspect, the acquired brain injury may be a traumatic brain injury. For example, the traumatic brain injury may be sustained during contact sport, military activities, or motor vehicle or other accidents. In particular embodiments, the traumatic brain injury may be mild traumatic brain injury, chronic traumatic encephalopathy, or concussion. In other embodiments, the acquired brain injury may comprise stroke.

Typically the cognitive decline comprises a decline in attention, learning, memory or executive function associated with the acquired brain injury.

In an embodiment, the trehalose is administered orally. For example, the trehalose may be formulated in a food, food supplement or beverage. In an exemplary embodiment the beverage may comprise a sports drink or carbonated beverage. In a further exemplary embodiment, the food supplement may comprise a tablet, such as an effervescent tablet, a powder or a gel.

In an exemplary embodiment, the trehalose may be administered at about 2% w/v in a suitable vehicle.

A third aspect of the present disclosure provides a method for inducing or increasing neuroplasticity in a subject, the method comprising administering to the subject an effective amount of trehalose.

In an embodiment, the subject is at risk of brain injury or of developing a neurodegenerative disease or mental illness. In a further embodiment the subject has sustained a brain injury, is elderly or is a patient with a neurodegenerative disease or mental illness.

The brain injury may be an acquired brain injury, such as a traumatic brain injury or stroke. In an exemplary embodiment the acquired brain injury is a traumatic brain injury. The traumatic brain injury may be mild traumatic brain injury, chronic traumatic encephalopathy, or concussion.

The neurodegenerative disease may be, for example, Alzheimer's disease, Parkinson's disease or Amyotrophic Lateral Sclerosis. The mental illness may comprise depression or anxiety.

In an embodiment, neuroplasticity comprises alterations in neurogenesis or synaptic plasticity. In exemplary embodiments, neurogenesis and/or synaptic plasticity are increased following administration of the trehalose.

A fourth aspect of the present disclosure provides use of trehalose in the manufacture of a composition or medicament for preventing or treating cognitive decline associated with brain injury in a subject.

In exemplary embodiments, the composition or medicament may be formulated in or as a food, food supplement, or a beverage.

A fifth aspect of the present disclosure provides use of trehalose in the manufacture of a composition or medicament for inducing or increasing neuroplasticity in a subject.

In an embodiment, the subject is a subject at risk of brain injury or of developing a neurodegenerative disease or mental illness. In a further embodiment the subject has sustained a brain injury, is elderly or is a patient with a neurodegenerative disease or mental illness.

BRIEF DESCRIPTION OF THE DRAWINGS

Aspects and embodiments of the present disclosure are described herein, by way of non-limiting example only, with reference to the following drawings.

FIG. 3: Trehalose confers cognitive benefits in the Y maze. Trehalose post-treated mice showed a significant overall frequency of visitation preference for the novel arm (red) over the start arm (black) compared to SSV treated littermates at both one-minute (a) (**$p<0.001$), and five-minute frequency (b) time points (*$p<0.01$). Additionally, trehalose treated mice spent a significantly greater duration of time in the novel arm at the one-minute (c) (**$p<0.001$) time point when compared to SSV controls. Pre-treated trehalose mice also performed significantly better than SSV littermates in the one (a) and five (b) minute frequency and one minute duration (c) assessments in the Y-maze. Trehalose pre-treated mice also significantly outperformed both the trehalose post-treatment and SSV treated mice in the five-minute duration assessment (d). Subsequent y-maze revealed that maltose treated mice had no significant preference for the novel arm at both the one-minute (e) or five-minute (f) frequency measurements when compared to SSV treated littermates.

DETAILED DESCRIPTION

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, typical methods and materials are described.

The articles "a" and "an" are used herein to refer to one or to more than one (i.e., to at least one) of the grammatical object of the article. By way of example, "an element" means one element or more than one element.

In the context of this specification, the term "about" is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

As used herein, the term "subject" may be used interchangeably with the term "individual" or "participant". A "subject" may include any mammal, such as humans, non-human primates, livestock animals (eg. sheep, pigs, cattle, horses, donkeys, goats), laboratory test animals (eg. mice, rabbits, rats, guinea pigs, other rodents), companion animals (eg. dogs, cats). In an exemplary embodiment, the subject is a human. In a further exemplary embodiment, the subject is a companion animal, such as a dog.

The terms "promoting" and "inducing", and variations thereof such as "promotion" and "inducement", as used herein do not necessarily imply the complete promotion or inducement of the specified event, activity or function. Rather, the promotion or inducement may be to an extent, and/or for a time, sufficient to produce the desired effect. The promotion or inducement of neuroplasticity, which may comprise neurogenesis or synaptic plasticity, by trehalose may be direct or indirect and may be in magnitude and/or be temporal in nature.

As used herein the term "effective amount" includes within its meaning a non-toxic but sufficient amount or dose of an agent or compound to provide the desired effect. The exact amount or dose required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein the terms "treating", "treatment", "preventing" and "prevention" refer to any and all uses which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery. In conditions which display or are characterized by multiple symptoms, the treatment or prevention need not necessarily remedy, prevent, hinder, retard, or reverse all of said symptoms, but may prevent, hinder, retard, or reverse one or more of said symptoms. In the context of some disorders, methods of the present disclosure involve "treating" the disorder in terms of reducing or ameliorating the occurrence of a highly undesirable event associated with the disorder or an irreversible outcome of the progression of the disorder but may not of itself prevent the initial occurrence of the event or outcome. Accordingly, treatment includes amelioration of the symptoms of a particular disorder or preventing or otherwise reducing the risk of developing a particular disorder.

The studies exemplified herein demonstrate that mice receiving a controlled cortical impact traumatic brain injury (TBI) and treated for one month with trehalose showed an overall significant improvement in the Morris water maze, Y-maze and open field behavioural tests compared to controls. Moreover, the inventors have surprisingly demonstrated upregulation of synaptophysin, doublecortin and brain derived neurotrophic factor (BDNF) protein in the contralateral cortex of trehalose treated mice, indicative of trehalose inducing neurogenesis and enhanced synaptic activity. The upregulation of BDNF has previously been shown to alleviate post-TBI depression in rodent models and is associated with improved brain function in ageing, neurodegenerative disease and other conditions. In light of the inventors' novel findings, the present disclosure contemplates trehalose as a potential treatment or preventative measure for TBI and associated cognitive dysfunction or decline. Embodiments of this disclosure contemplate the administration of trehalose to patients with TBI and subjects at risk of TBI, either as a monotherapy or in conjunction with other treatment alternatives.

Accordingly, one aspect of the present disclosure provides a method for preventing or reducing cognitive dysfunction or decline associated with an acquired brain injury in a subject, the method comprising administering to the subject a therapeutically effective amount of trehalose.

Another aspect provides a method for treating cognitive dysfunction or decline associated with an acquired brain injury in a subject, the method comprising administering to the subject a therapeutically effective amount of trehalose.

The inventors' also describe herein for the first time neurogenesis and enhanced synaptic activity following trehalose treatment in a rodent model of neurodegeneration. The combined data in the examples presented herein suggest that two different disease models (traumatic brain injury and neurodegeneration) share a unique and previously unreported significantly enhanced expression of synaptophysin and doublecortin after trehalose treatment. Without wishing to be bound by theory, the inventors suggest that neuroplasticity may be a novel mechanism of action of trehalose.

Accordingly, another aspect of the present disclosure provides a method for inducing or increasing neuroplasticity in a subject, the method comprising administering to the subject an effective amount of trehalose.

Subjects at risk of an acquired brain injury, in particular at risk of traumatic brain injury include, for example, those participating in a sport with an occurrence of concussions, such as football players, boxers and mixed martial arts fighters. Other subjects at risk of traumatic brain injury include combatants in armed conflicts, or undergoing dangerous or extreme sporting or adventure activities.

In the context of the present specification, the term "acquired brain injury" is used to refer to damage to the brain that occurs after birth and is not, of itself, related to a congenital or degenerative condition. Thus, acquired brain injury includes traumatic brain injury, which occurs when the brain sustains damages from a sudden trauma. Traumatic brain injury may comprise mild traumatic brain injury, chronic traumatic encephalopathy, or concussion. The severity of a traumatic brain injury can vary from mild to moderate or severe and symptoms may appear immediately or within days, weeks, months or years after the traumatic event. Symptoms of traumatic brain injury may include headache, confusion, dizziness, changes in mood, and impairment in cognitive function, such as memory, learning, and attention, nausea, convulsions or seizures, slurring of speech, numbness of extremities, and loss of coordination. Stroke, hypoxic-ischemia, haemorrhage, encephalitis, and related acquired encephalopathies are other exemplary forms of brain injury in the context of the present disclosure.

As used herein, the terms "cognitive dysfunction" and "cognitive decline" describe abnormal or decreasing cognitive function compared to one or more control subjects or compared to the cognitive function of the subject at an earlier point in time. Cognitive function may comprise, for example, attention, learning, memory, affect or executive function, such as judgement, reasoning, planning, problem solving and decision making. Methods of assessing cognitive function are well known to those skilled in the art.

Use of the term "associated with" herein describes a relationship between the occurrence of an event with an action or measure. Thus, in the context of cognitive dysfunction or decline associated with an acquired brain injury means that the cognitive dysfunction or decline results from, either directly or indirectly, the brain injury. The cognitive dysfunction or decline may occur or begin at the time of the brain injury. Alternatively, the brain injury and the cognitive dysfunction or decline may be temporally spaced such that the cognitive dysfunction or decline may occur or begin, minutes, hours, days, weeks, months or years after the occurrence of the brain injury. Thus, symptoms of cognitive dysfunction or decline may not be apparent until hours, days, weeks, months or years after a brain injury event.

As used herein, the term "neurodegenerative disease" refers to a disease wherein there is progressive loss in the structure or function of neurons. Exemplary neurodegenerative diseases include, but are not limited to Alzheimer's disease, Parkinson's disease; fronto-temporal dementia (FTD) and other tauopathies, amyotrophic lateral sclerosis and Huntington's disease.

As used herein the term "neuroplasticity" refers to changes in the structure or function of the brain, including to neurons. Neuroplasticity may include the generation of new neurons (neurogenesis) or alterations to the structure, function or activity of cells within the brain or of individual or groups of synapses (synaptic plasticity). For example, new synapses may be formed, altered or receptor density or location may be modified to result in plasticity. Neuroplasticity may be associated with changes in growth factors such as brain derived neurotrophic factor (BDNF). One skilled in the art will appreciate that there are many biological markers that may be measured to assess neuroplasticity, including doublecortin to measure neurogenesis, and synaptophysin to measure synaptic activity.

Trehalose has a generous human safety profile and is an FDA approved excipient in many pharmaceuticals. Accordingly, means for employing trehalose, and identifying suitable (e.g. safe and convenient) dosages of trehalose is well within the experience and expertise of the skilled addressee. Any suitable amount or dose of trehalose may be administered to a subject in accordance with the present disclosure. The effective amount or therapeutically effective amount for any particular subject may depend upon a variety of factors including: the type of acquired brain injury suffered or to which the subject is at risk, and the severity of the brain injury; the composition employed; the age, body weight, general health, sex and diet of the subject; the time of administration; the route of administration; the rate of sequestration; the duration of the treatment; other agents used in combination or coincidental with the treatment, together with other related factors well known in medicine. One skilled in the art would be able, by routine experimentation, to determine an effective, non-toxic amount of trehalose to be employed.

The skilled addressee will recognise that in determining an appropriate and effective dosage range for administration to humans based on the mouse studies exemplified herein, dose escalation studies would be conducted. The skilled addressee would therefore appreciate that the above mentioned doses and dosage ranges are exemplary only based on the doses administered in the mouse studies exemplified herein, and the actual dose or dosage range to be employed in humans may be varied depending on the results of such dose escalation studies. Based on the data exemplified herein, the appropriate and effective dose or dosage range to be administered to humans can be determined by routine optimisation, without undue burden or experimentation.

Those skilled in the art will appreciate that single or multiple administrations of trehalose or, compositions, containing trehalose, can be carried out in accordance with the present disclosure with dose levels and dosing regimes being determined as required depending on the need of the subject and on the condition of the subject to be treated. The skilled addressee can readily determine suitable dosage regimes. Those skilled in the art will appreciate that suitable rates of administration will depend on a number of factors such as the particular composition being administered including the form in which the composition is administered, the age, body weight, general health, sex and dietary requirements of the subject, as well as any drugs or agents used in combination or coincidental with the compositions. For example, several divided doses may be administered hourly, daily, weekly, monthly or at other suitable time intervals or the dose may be proportionally reduced as indicated by the exigencies of the situation. Based on the teaching herein those skilled in the art will, by routine trial and experimentation, be capable of determining suitable dosage regimes on a case-by-case basis.

Trehalose may be administered by any suitable route, including orally, for example, in a composition with an inert diluent or with an assimilable edible carrier, or incorporated directly into the diet. For oral administration, the trehalose may be incorporated with excipients and used in the form of tablets, ingestible tablets, buccal tablets, troches, capsules, elixirs, suspensions, syrups, wafers, and the like. Suitable oral dosage forms may also include liquids, granules, powders, gels, pastes, soluble sachets, orally soluble forms, caplets, lozenges, effervescent tablets, chewable tablets, multi-layer tablets, and the like.

The amount of trehalose in such therapeutically useful compositions is such that a suitable dosage will be obtained. Compositions or preparations according to embodiments of the present disclosure may be prepared so that an oral dosage unit form contains between about 50 mg and about 1000 mg trehalose per kg body weight, or between about 50 mg and about 500 mg trehalose per kg body weight. By way of example, a composition may be formulated to deliver about 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 275 mg, 300 mg, 325 mg, 350 mg, 375 mg, 400 mg, 425 mg, 450 mg, 475 mg, or 500 mg trehalose per kg body weight. In an exemplary embodiment, the composition may be formulated to deliver about 167 mg trehalose per kg body weight.

Compositions comprising trehalose may include any suitable additives, carriers, additional therapeutic agents, bioavailability enhancers, side-effect suppressing components, diluents, buffers, flavouring agents, binders, preservatives or other ingredients that are not detrimental to the efficacy of the composition. Such compositions can be readily manufactured by those skilled in the art using known techniques and processes well known in the pharmaceutical and nutritional and nutraceutical industries and may be suitably formulated for oral administration.

Tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the oligonucleotides may be incorporated into sustained-release preparations and formulations.

Trehalose and compositions comprising trehalose may be conveniently incorporated in a variety of beverages, food products, nutraceutical products, nutritional supplements, food additives, pharmaceuticals and over-the-counter formulations, as exemplified hereinbelow. However those skilled in the art will appreciate that the compositions may be formulated and provided to users in any suitable form known in the art.

The trehalose and compositions comprising trehalose may be conveniently incorporated in a variety of beverage products. Specific examples of suitable types of beverages into which trehalose, or compositions comprising trehalose, may be incorporated for administration in accordance with the present disclosure include, but are not limited to water, carbonated beverages, sports drinks, nutritional beverages, fruit juice, vegetable juice, milk, and other products that are water-based, milk-based, yoghurt-based, other dairy-based, milk-substitute based (such as soy milk or oat milk) or juice-based beverages. The trehalose, or composition comprising trehalose may be provided in powder, granule or other solid form to be added to the beverage by the user, or premixed in the beverage, or may be provided as a concentrated liquid, gel or paste form to be added to a suitable beverage. Alternatively, the composition may be provided to the user in a liquid form, premixed with a suitable beverage. In one exemplary embodiment the composition may be included in a water-based drink (such as a sports drink) between about 0.5% and about 10% w/v, depending on the exact nature and volume of the drink. In further exemplary embodiments, the trehalose may be provided at about 0.5%, about 1%, about 1.5%, about 2%, about 2.5%, about 3%, about 3.5%, about 4%, about 4.5%, about 5%, about 5.5%, about 6%, about 6.5%, about 7%. about 7.5%, about 8%, about 8.5%, about 9%, about 9.5% or about 10% w/v. In an exemplary embodiment, the trehalose may be provided at about 2% w/v.

Trehalose and compositions comprising trehalose may also be conveniently incorporated in a variety of food products, nutraceutical products, or food additives. The food product or food additive may be a solid form such as a powder, or a liquid form. Suitable food products may include baked products such as crackers, breads, muffins, rolls, bagels, biscuits, cereals, bars such as muesli bars, health food bars and the like, dressings, sauces, custards, yoghurts, puddings, pre-packaged frozen meals, soups and confectioneries.

In another embodiment, trehalose may simply be consumed as a powder, granules, gel, paste, solid dosage form or concentrated liquid form in the absence of an additional beverage or food product. Those skilled in the art will appreciate that many oral delivery systems may be employed depending on the identity and tolerances of the subject.

Methods of the present disclosure may be employed in combination with other therapies and treatments known to those skilled in the art for the treatment of acquired brain injury, for the treatment or prevention of cognitive dysfunction or cognitive decline associated with acquired brain injury, or for inducing or promoting neuroplasticity. For such combination therapies, each component of the combination may be administered at the same time, or sequentially in any order, or at different times, so as to provide the desired therapeutic effect. When administered separately, it may be preferred for the components to be administered by the same route of administration, although it is not necessary for this to be so. Alternatively, the components may be formulated together in a single dosage unit as a combination product.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present disclosure will now be described with reference to the following specific examples, which should not be construed as in any way limiting the scope of the disclosure.

EXAMPLES

The following examples are illustrative of the disclosure and should not be construed as limiting in any way the general nature of the disclosure of the description throughout this specification.

General Methods

All procedures were carried out in accordance with protocols approved by the Howard Florey Animal Ethics Committee and were conducted in accordance with the Australian Code of Practice for the Care and Use of Animals for Scientific Purposes as described by the National Health and Medical Research Council of Australia.

Trehalose

Trehalose (Sigma) has a generous safety profile in rodents and humans has been posted as "Generally Regarded as Safe" (GRAS) for human consumption by the U.S. Federal Drug Administration (FDA) in October 2000, is used as a food additive, and is also an excipient in many pharmaceuticals, making trehalose a safe, natural and pharmaceutically accepted product. In this study, it was supplied as a 2% w/v in standard suspension vehicle (SSV) solution via oral gavage at a dose of 0.1 ml to 10 g body weight. SSV solution was purchased from Sigma and contains 0.9% sodium chloride (NaCl), 0.5% Sodium carboxymethylcellulose (Na-CMC), 0.5% Benzyl alcohol, 0.4%, Tween 80 (polyoxyethylenesorbitan monooleate).

Animals and Surgical Procedures

Surgical procedures and controlled cortical impact (CCI) have been previously described (see Portbury et al., 2015, *Metallomics*. doi:10.1039/c5mt00234f). Briefly, 3 month-old male C57B16 mice were anesthetized via intraperitoneal injection of 100 mg/kg ketamine and 10 mg/kg xylazine. A 10 mm mid-line incision was made over the skull, and the skin and fascia were reflected to make a 4 mm craniotomy on the central aspect of the right parietal bone using a motorized drill. Upon animal positioning in a stereotaxic frame a CCI injury was subsequently delivered (3 m/s velocity with a 1.5 mm penetration depth).

Three groups of animals were subjected to TBI as separate experiments. The first group of animals were treated daily with 2% trehalose in SSV solution at 0.1 ml per 10 g body weight via oral gavage for a period of 31 days or SSV solution following the TBI. The mice on average weighed 20 to 25 g, and hence received 200 μl to 250 μl of a 2% solution. The second groups of animals underwent an identical dosing procedure but were treated with either SSV or maltose as a disaccharide control for trehalose. A third group of animals that did not undergo any behavioural assessment, was used for LA-ICPMS metal analysis. A further group of animals was pre-treated with trehalose prior to TBI. These pretreated mice received a daily treatment of 2% trehalose in SSV solution at 0.1 ml per 10 g body weight via oral gavage for 7 days prior to TBI. Following TBI, these animals received SSV solution only for the remaining duration of the experiment.

Laser Ablation Inductively Coupled Plasma Mass Spectrometry

A comprehensive description of laser ablation-inductively coupled plasma mass spectrometry (LA-ICPMS) procedure of TBI mouse tissue has been previously published [21]. Briefly, Trehalose treated and non-treated animals (n=5 per group) were euthanized at 24 hr, 72 hr, 7 day, 14 day and 28 day-post TBI surgeries. Tissue was prepared as previously described and was subjected to LA-ICPMS.

Cognitive Behavior Assessment

The Morris Water Maze (MWM) was used to assess the effect of trehalose on spatial learning and memory function following TBI. The pre-training acclimation day of the water maze was performed on day 23 of dosing, followed by six days of place discrimination training of four 90 second trials per day, conducted on days 24-29 of dosing. The probe trial was performed 24 hours after training on dosing day 30 to assess retention of the task. Data was analysed using the Ethovision automated tracking system. Animals were culled on day 31. Both experimental groups adhered to the same time lines of behavioral assessment. The open field assessment was performed on day 19 of dosing and the Y-maze assessment was performed on day 21 of dosing.

Western Blot Analysis

For the behaviorally assessed animals the cortex and hippocampus of both ipsilateral and contralateral hemispheres were homogenized in 15 volumes of ice-cold PBS containing Complete Protease Inhibitor Cocktail tablets (Roche Applied Science, Indianapolis, Ind., USA) and subsequently centrifuged (100,000×g) for 30 minutes at 4° C. Supernatant was removed to yield the soluble fraction (S1). Remaining pellet underwent further extraction via 30 minutes of vigorous agitation in above mentioned homogenization buffer containing 2% (vol/vol) Triton X100. Insoluble material was pelleted via centrifugation (20,000×g) for 20 minutes, and supernatant was retained as the membrane fraction (P1). Protein concentrations were determined using Pierce BCA protein assay (Pierce Biotechnology, Rockford, Ill., USA) to ensure equal loading of 10 μg protein samples on gel. Samples were prepared for PAGE by the addition of 4× protein sample loading buffer (LICOR, Lincoln, Nebr., USA) and 10× NuPAGE sample reducing agent (to a final 1× concentration). Samples were heated to 70° C. for 10 min, loaded onto Bolt 4-12% Bis-Tris Plus gels (Invitrogen-Life Technologies, Grand Island, N.Y., USA) along with Licor One-Color protein molecular weight markers (LICOR, Lincoln, Nebr., USA) and run at 125 V for 60 min in appropriately diluted Bolt MES SDS 20× running buffer (Invitrogen-Life Technologies, Grand Island, N.Y., USA). Gels were transferred to Immobilon—PF, PVDF membrane (Millipore) using the Invitrogen Bolt wet-gel Transfer Device (Invitrogen-Life Technologies, Grand Island, N.Y., USA) at 15 V for 60 min in appropriately diluted 20× Bolt transfer buffer (Invitrogen-Life Technologies, Grand Island, N.Y., USA). Membranes were blocked in tris-buffered saline with tween 20 (TBST) containing 5% skim milk powder and then incubated with primary antibody overnight at 4° C. Blots were rinsed in TBST and incubated with appropriate secondary antibody (1 h, RT), followed by further rinsing and imaged using a LI-COR Odyssey Imaging system (LI-COR Biosciences, Lincoln Nebr., USA), and analysed with Image Studio Lite software (LI-COR Biosciences, Lincoln Nebr., USA). Sample data were normalized to total protein loaded and to the GAPDH or β-actin loading control.

Statistical Analysis

For LA-ICPMS samples, statistical analysis was carried out in Prism 7 (Graph-Pad) software. Analysis was carried out with a two-tailed t test with the level of significance set at p=0.05. For multiple comparisons two-way ANOVA was used to identify significant differences between ipsilateral and contralateral ROI's. For western blot analysis, images were produced using Image Studio Lite (version 4.0.21, LI-COR Biosciences) and subsequent statistical analysis was carried out in Prism 7 (Graph-Pad). All behavioral analysis was performed using Prism 7 (Graph-Pad).

Figure 1:
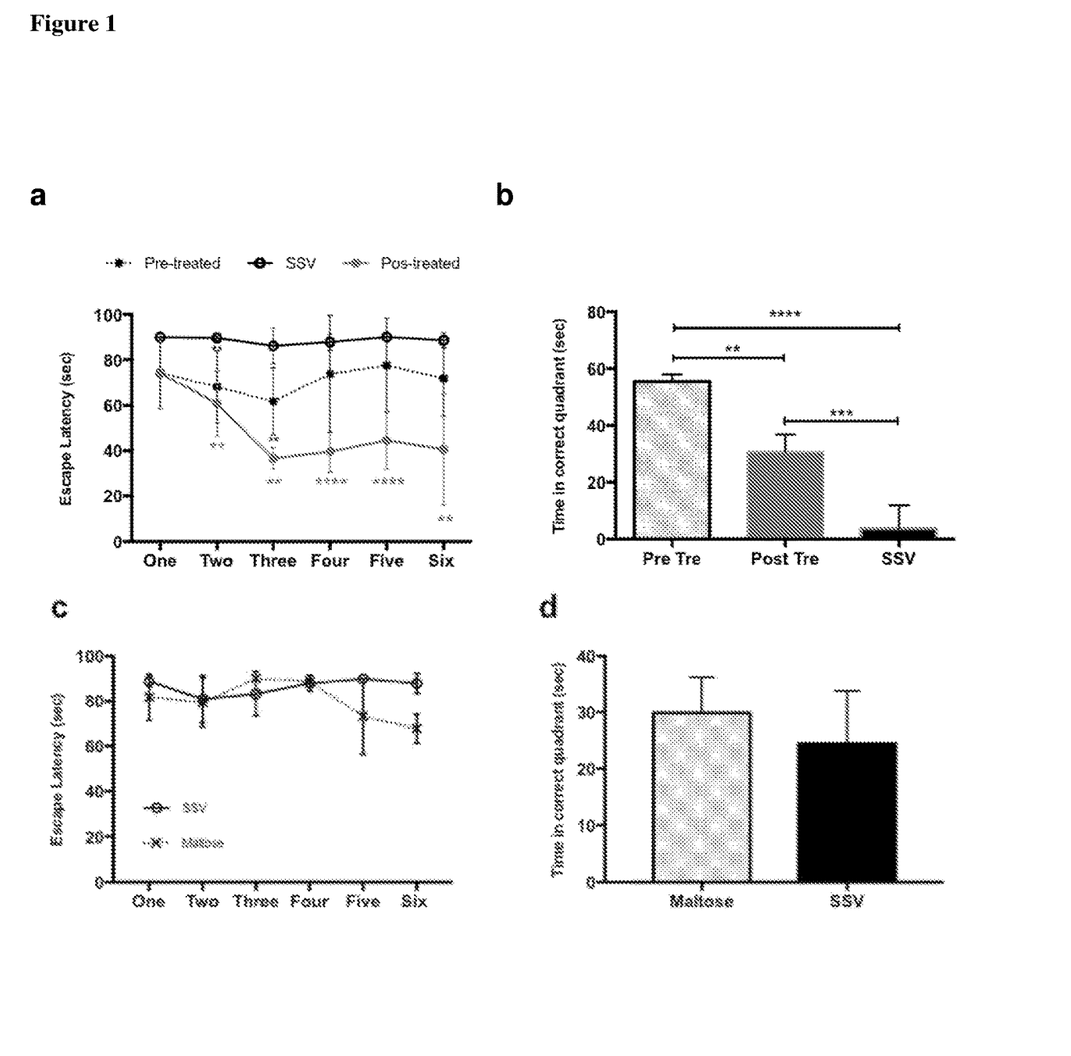
FIG. 1: Trehalose improves performance of brain injured mice in the Morris water maze. Brain injured mice treated post-injury with trehalose revealed an overall significant performance improvement (2 way ANOVA P<0.00001) in the learning (a) and recall (b) components of the Morris water maze. Subsequent water maze with maltose treated brain-injured animals revealed no such improvement in the learning (c) or recall (d) components. Mice pre-treated with trehalose outperformed SSV controls in the learning (a) component of the trial, although not significantly. Mice pre-treated with trehalose did, however significantly outperform trehalose post-treated mice and SSV controls in the recall (b) component of the trial, as did the trehalose post-treated mice.

Example 1—Trehalose Restores Water Maze Performance Following Traumatic Brain Injury A significant overall improvement in escape latency was observed in the Morris water maze (MWM) test for trehalose treated mice when compared to control treatment group post TBI. Trehalose treated mice (n=5) demonstrated an overall increased acquisition of the task (ANOVA, $p<0.0001$) as compared with SSV—treated control group (n=8) (FIG. 1a). Additionally, the probe day twenty-four-hour retention task revealed a significant improvement in memory in trehalose treated animals (P=0.0159) (FIG. 1b). The second TBI control group consisting of the dissacharide maltose control group (n=7) revealed no significant differences in escape latency between the maltose treated group and SSV treated (n=13) (FIG. 1c) or the probe day 24-hour task retention (FIG. 1d).

To determine whether trehalose administration may prevent traumatic brain injury-related decline in cortical function and behaviours, the inventors treated a group of mice with trehalose prior to TBI. Trehalose pre-treated mice received a daily 2% oral gavage dose of trehalose for a period of one week prior to the controlled cortical impact injury, after which they received only vehicle solution. Mice pre-treated with trehalose outperformed SSV controls in the learning (FIG. 1a) component of the water maze trial, although not significantly. Mice pre-treated with trehalose did, however significantly outperform trehalose post-treated mice and SSV controls in the recall (FIG. 1b) component of the trial.

Example 2—Trehalose Increases Spontaneous Activity in the Open Field Assessment

Figure 2:
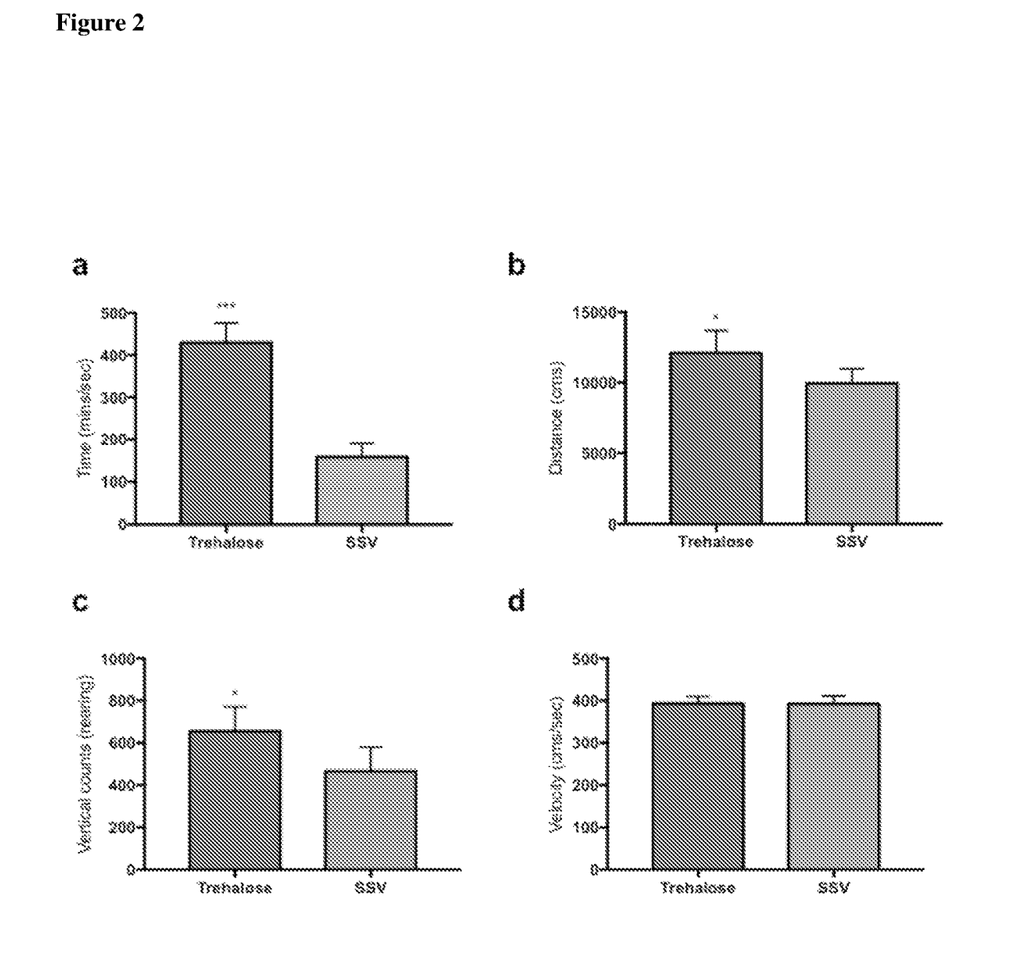
FIG. 2: Trehalose treated mice show significantly enhanced willingness to explore in the open field anxiety test. Post-TBI treated mice showed a significant reduction in anxiety and an increased willingness to explore when compared to SSV littermates. Post-treated mice showed a significant increase in ambulatory time (****$p<0.00001$) (a), ambulatory distance (*$p<0.01$) (b), vertical counts (*$p<0.01$) (c) without a significant increase in velocity (d).

Open field behavioural assessment indicated a significant increase in exploration activity for the trehalose treated group compared to control group in ambulatory time (P<0.001) (FIG. 2a), total ambulatory distance (P<0.01) (FIG. 2b) and vertical counts (P<0.01) (FIG. 2c). Importantly, there was no significant difference in ambulatory velocity between the two groups (FIG. 2d). The secondary control group treated with maltose was not tested in the open field assessment.

In the open field test, there was a significant increase in locomotion and exploration in the trehalose treated group when compared to controls after TBI. The open field test is an accepted paradigm for measuring anxiety and depression in rodents, whereby an increase in locomotion and exploration are believed to be representative of a lower level of anxiety and depression. Additionally, the observed enhanced activity in the open field environment was more than likely not due to an increased speed or hyperactivity related to trehalose effect, indicated by equality in ambulatory speed between groups.

Example 3—Trehalose Enhances Cognitive Performance of TBI Mice in the Y-Maze

Figure 3:
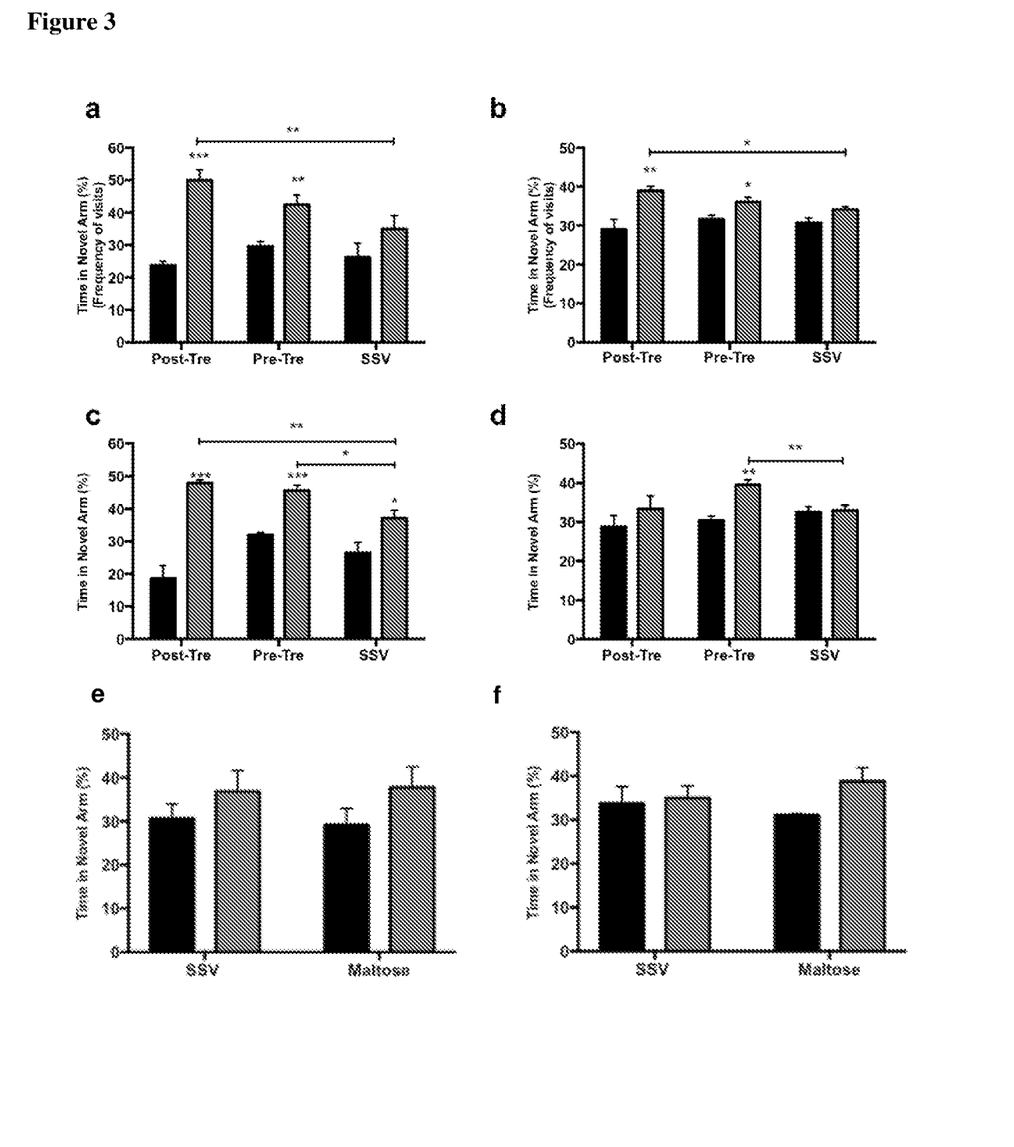

In the y-maze, the mice treated with trehalose post-TBI showed an overall significant improvement in both the duration and frequency of visits into the novel arm, indicating a willingness to explore a new environment. One-minute frequency was significantly enhanced over the SSV group (p<0.001) (FIG. 3a) as was the five-minute frequency (p<0.01) (FIG. 3b). Additionally, trehalose treated mice had a significant overall duration of time in the novel arm at the one-minute time point (p<0.001) (FIG. 3c). In the subsequent control study, the maltose control group was unremarkable compared to the SSV group yielding no significant improvement in one (FIG. 3e) or five (FIG. 3f) minute frequency or one-minute (data not shown) duration time points.

In a y-maze, both pre-treated trehalose mice also performed significantly better than SSV-treated littermates in the one (FIG. 3a) and five (FIG. 3b) minute frequency and one minute duration (FIG. 3c) assessments in the y-maze. Trehalose pre-treated mice also significantly outperformed both the trehalose post-treatment and SSV treated mice in the five-minute duration assessment. These studies demonstrate that pre-treatment with trehalose is likely just as effective (if not more so) on post-injury function and behaviour as treatment received after an injury.

Results therefore indicated that trehalose administration greatly improved working spatial memory performance following TBI in both the Morris water maze and the y-maze.

Example 4—Biological Transition Metals and TBI

LA-ICPMS revealed no significant overall change in zinc concentration between trehalose and SSV treatment groups in any region observed in either the ipsilateral or contralateral cortex of mice treated after TBI. Neither were there any significant intra-day changes in zinc between the trehalose and SSV treatment group (data not shown).

Whilst no overall change in copper concentration was observed in any region analyzed, mice treated with trehalose post-TBI revealed significant intra-day increases at day 7 in the ipsilateral ROI1, ROI2 and also at day 7 in the entire ipsilateral hemisphere (data not shown) that was not observed in SSV treated mice. Similarly, at day 7 in the contralateral ROI3 and the entire hemisphere there was a significant increase in copper concentration.

LA-ICPMS revealed subtle changes in the iron profile over the time course in mice treated post-TBI. In every region analyzed on the ipsilateral side from day seven to fourteen there is a decrease in iron for the SSV treated group. Conversely there was an increased trend in iron for the trehalose treated group at the same time-points, with a significant increase observed in the ipsilateral ROI1 at day 14 between trehalose and SSV (data not shown). Comparatively, the contralateral side reflects an almost identical pattern except for ROI2 where the SSV treated day fourteen concentrations is not decreased from day seven. However, there was a significant increase in iron at day fourteen in the entire contralateral hemisphere. Overall, the iron concentrations in all ipsilateral regions are greater than the contralateral regions.

Example 5—Trehalose does not Significantly Change Cortical Tissue Loss

Volumetric analysis of trehalose treated animals in this study revealed no difference in cortical tissue loss when compared to controls (data not shown), suggesting that tissue preservation by trehalose treatment after injury was not responsible for the behaviour benefits observed.

Autophagy enhancement, a known consequence of trehalose treatment, was assessed via LC3 western blot detection (data not shown). A significant enhancement in autophagy between trehalose, SSV and maltose treated groups was not detectable. Previous studies have shown autophagy to be naturally elevated in TBI, with one study showing LC3 greatly elevated at 32 days post TBI.

Example 6—Markers of Neurogenesis, Synaptogenesis and Growth are Increased by Trehalose after Brain Injury Protein extracted from brain tissue was used to assess the synaptic vessel associated protein synaptophysin as a marker of synaptic activity, the neuronal migration protein doublecortin (DCX) to assess the presence of neurogenesis, as well as brain derived neurotrophic factor (BDNF) and Pro-BDNF to assess nerve growth and synaptic remodeling.

Figure 4:
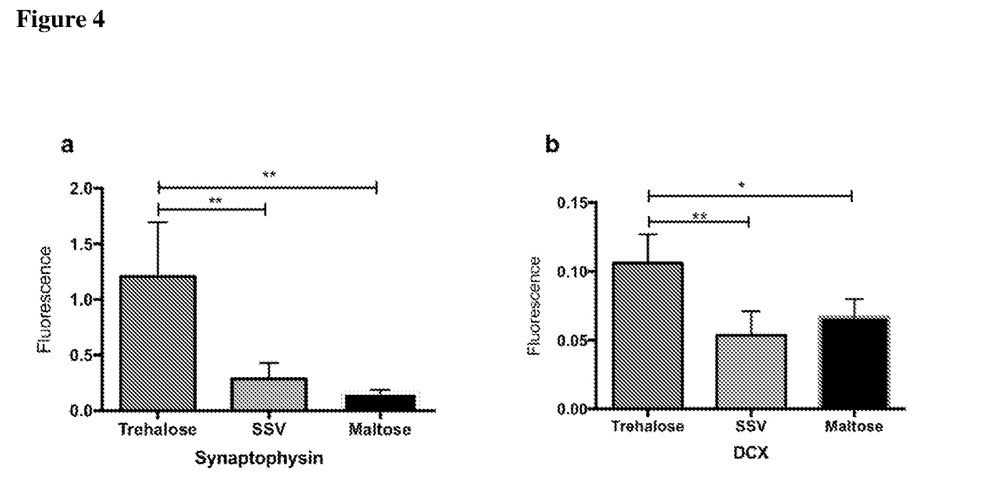
FIG. 4: Trehalose increases synaptophysin and DCX in the contralateral cortex. Trehalose significantly increased synaptophysin protein in the contralateral cortex over SSV (*$p<0.0221$) and maltose (*$p<0.0193$) controls (a). Trehalose significantly increases DCX in the contralateral cortex compared to SSV (*$p<0.0147$) and maltose (*$p<0.0123$) controls (b).

Mice treated with trehalose post-TBI showed a significantly elevated expression of the synaptic vesicle protein synaptophysin in the contralateral cortex when compared to SSV and maltose treated controls at 31 days post-TBI (FIG. 4a). The elevation of synaptophysin was unique to the contralateral cortex with no significant elevation observed in the contralateral hippocampus, or the ipsilateral cortex and hippocampus. However, the ipsilateral hippocampus did see a non-significant elevation of synaptophysin for the trehalose treated group when compared to control groups.

DCX protein analysis revealed an identical profile, whereby there was a significant increase of DCX protein observed in the contralateral cortex for trehalose treated animals (FIG. 4b) and an absence of elevated DCX in the contralateral hippocampus or ipsilateral cortex and hippocampus when compared to control groups. DCX expression in the ipsilateral cortex and hippocampus of trehalose treated mice were both significantly decreased compared to SSV and maltose controls.

Figure 5:
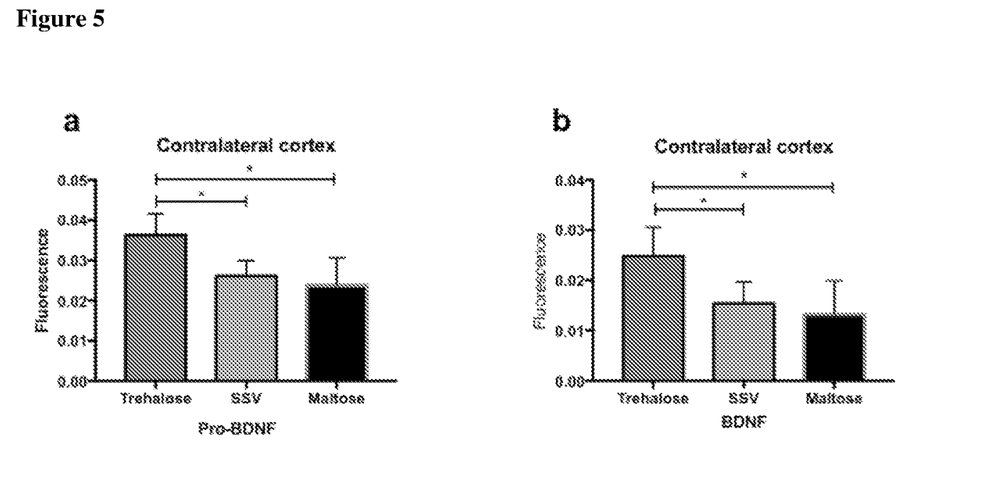
FIG. 5: Trehalose increases Pro-BDNF and BDNF in the contralateral cortex. Trehalose significantly increased Pro-BDNF protein in the contralateral cortex over SSV (*$p<0.0210$) and maltose (*$p<0.0287$) controls (a). Trehalose also significantly increased BDNF protein in the contralateral cortex over SSV (*$p<0.0296$) and maltose (*$p<0.0255$) controls.

Similarly, trehalose treated animals revealed a significant increase in both pro-BDNF (FIG. 5a) and BDNF (FIG. 5b) in the contralateral cortex when compared to SSV and maltose treated littermates. Both BDNF and pro-BDNF was not significantly elevated in the contralateral hippocampus or ipsilateral cortex and hippocampus. BDNF is a neurotrophic factor that promotes growth and development of immature neurons and enhances the survival and functions of adult neurons in the central nervous system. BDNF has been shown to be upregulated during declarative memory formation in primate cortex, and endogenous BDNF is required for long-term memory formation in the rat parietal cortex.

Example 7—Trehalose Treatment Prevents Cognitive Decline and Promotes Neuroplasticity in a Model of Alzheimer's Disease The effects of trehalose treatment were also studied in Tg2576 transgenic mice, which model Alzheimer's disease and exhibit cognitive decline in aging. Transgenic Tg2576 mice were treated daily with 2% trehalose (0.1 ml/10 g body weight) in SSV (Sigma)(n=15, average age 16.2±3 months of age) via oral gavage or SSV (saline vehicle suspension) (n=12, 16±3 months of age). Mice were dosed for a period of 31 days, with the Morris water maze commencing on day 23 of dosing. Mice were culled on day 31, and DCX and synaptophysin expression were assessed.

Figure 6:
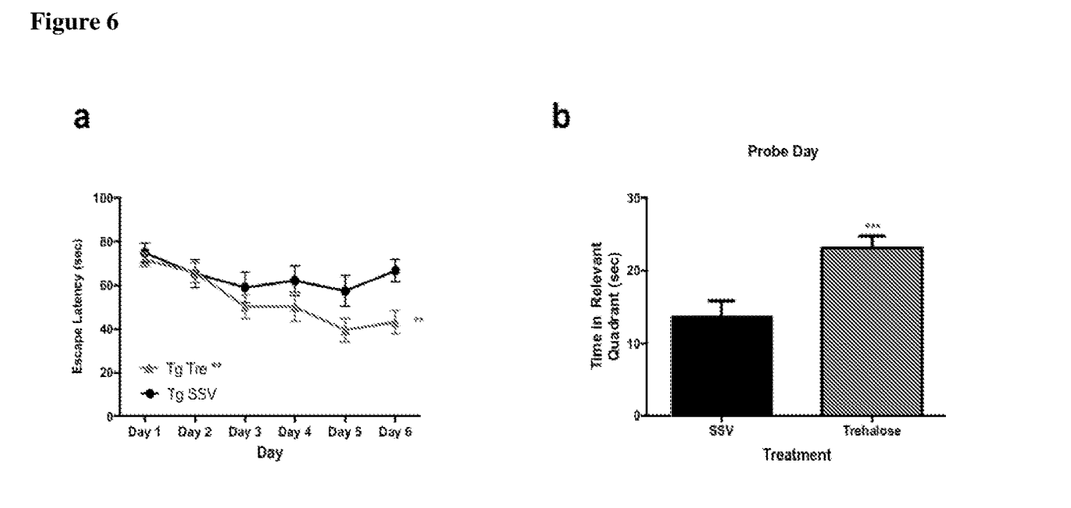
FIG. 6: Two-way ANOVA ($p<0.0012$) revealed a significant decrease in escape latency for Tg2576 trehalose treated mice compared to Tg2576 SSV treated litter mate controls over the course of the trial (a). Two-tailed t-test revealed a significant ($p<0.0003$) increase in time spent in the relevant quadrant for trehalose treated Tg2576 mice compared to SSV treated Tg2576 control littermates (b).

Trehalose treatment proved to be efficacious as a treatment to prevent cognitive decline as evidenced by significant cognitive improvement in the Morris water maze (FIG. 6).

Figure 7:
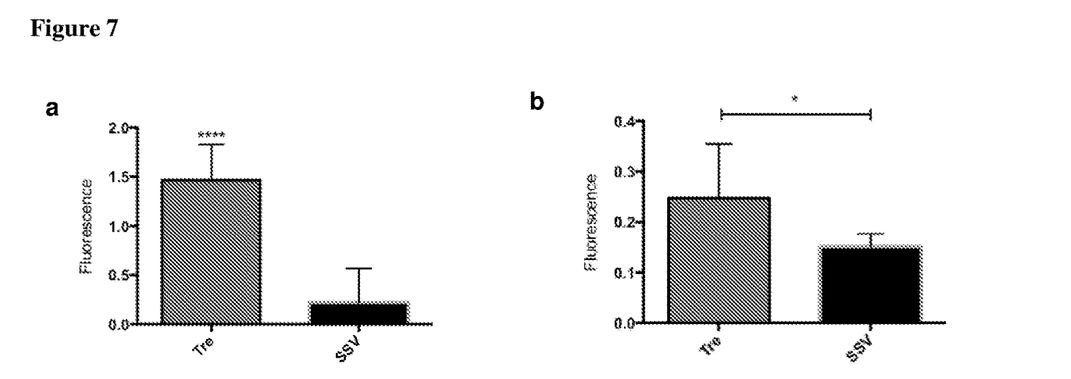
FIG. 7: Trehalose increases synaptophysin in the hippocampus of Tg2576 treated mice. Trehalose treated Tg2576 mice revealed a significant increase ($p<0.0001$) in synaptophysin protein expression in the hippocampus when compared to their SSV treated littermate controls (a). There was no significant difference observed in the cortex between trehalose and SSV treatment groups. Trehalose increases Doublecortin (DCX) expression in Tg2576 hippocampus. Unpaired t-test revealed a significant ($p<0.0401$) increase in DCX protein expression in trehalose treated Tg2576 hippocampus when compared to SSV treated littermate controls (b).

Expression of synaptophysin, a reliable synaptic marker indicative of synaptic activity, was also increased in the trehalose-treated Tg2576 mice relative to SSV-treated controls (FIG. 7a). Furthermore, doublecortin (DCX), a reliable marker of neurogenesis and synaptic remodelling, was also increased in the trehalose treated Tg2576 mice (FIG. 7b).

The invention claimed is:

1. A method for reducing cognitive dysfunction or decline associated with an acquired brain injury in a subject in need thereof, the method comprising administering to the subject a therapeutically effective amount of trehalose, wherein the trehalose is orally administered in a solution comprising at least about 2% trehalose (w/v) at a dosage selected from about 50 mg per kg body weight to about 1000 mg per kg body weight.

2. The method according to claim 1, wherein the subject is at risk of an acquired brain injury.

3. The method according to claim 1, wherein the subject has sustained an acquired brain injury.

4. A method for hindering or reversing cognitive dysfunction or decline associated with an acquired brain injury in a subject in need thereof, the method comprising orally administering to the subject a therapeutically effective amount of trehalose, wherein the trehalose is administered in a solution comprising at least about 2% trehalose (w/v) at a dosage selected from about 50 mg per kg body weight to about 1000 mg per kg body weight.

5. The method according to claim 1, wherein the acquired brain injury is a traumatic brain injury.

6. The method according to claim 5, wherein the traumatic brain injury is a mild traumatic brain injury according to the Glasgow Coma Scale, chronic traumatic encephalopathy, or concussion.

7. The method according to claim 1, wherein the cognitive decline comprises a decline in attention, learning, memory or executive function associated with the acquired brain injury.

8. A method for inducing or increasing neuroplasticity in a subject, the method comprising orally administering to the subject an effective amount of trehalose, wherein the trehalose is administered in a solution comprising at least about 2% trehalose (w/v) at a dosage selected from about 50 mg per kg body weight to about 1000 mg per kg body weight.

9. The method according to claim 8, wherein the subject is at risk of brain injury or of developing a neurodegenerative disease or mental illness.

10. The method according to claim 8, wherein the subject has sustained a brain injury, is elderly or is a patient with a neurodegenerative disease or mental illness.

11. The method according to claim 9, wherein the neurodegenerative disease is Alzheimer's disease, Parkinson's disease or Amyotrophic Lateral Sclerosis.

12. The method according to claim 9, wherein the mental illness comprises depression or anxiety.

13. The method according to claim 8, wherein the neuroplasticity comprises neurogenesis or synaptic plasticity.

14. The method according to claim 8, wherein neurogenesis and/or synaptic plasticity are increased following administration of the trehalose.

15. The method according to claim 1, wherein the trehalose is administered in a solution comprising about 2% to 10% trehalose (w/v).

16. The method according to claim 4, wherein the trehalose is administered in a solution comprising about 2% to 10% trehalose (w/v).

17. The method according to claim 8, wherein the trehalose is administered in a solution comprising about 2% to 10% trehalose (w/v).

* * * * *

UNITED STATES PATENT AND TRADEMARK OFFICE
CERTIFICATE OF CORRECTION

PATENT NO. : 11,602,538 B2
APPLICATION NO. : 16/497286
DATED : March 14, 2023
INVENTOR(S) : Paul Adlard et al.

Page 1 of 1

It is certified that error appears in the above-identified patent and that said Letters Patent is hereby corrected as shown below:

In the Specification

In Column 9, Line 16, please delete "7%." and replace it with -- 7%, --;

In Column 9, Line 54, please delete the extra word "that";

In Column 12, Line 5, please delete "dissacharide" and replace it with -- disac charide --.

Signed and Sealed this
Nineteenth Day of September, 2023

Katherine Kelly Vidal
*Director of the United States Patent and Trademark Office*